(12) United States Patent
Wisniewski et al.

(10) Patent No.: US 8,778,881 B2
(45) Date of Patent: *Jul. 15, 2014

(54) PEPTIDIC VASOPRESSIN RECEPTOR AGONISTS

(75) Inventors: Kazimierz Wisniewski, San Diego, CA (US); Claudio Schteingart, San Diego, CA (US); Regent LaPorte, San Diego, CA (US); Robert Felix Galyean, Escondido, CA (US); Pierre J.M. Riviere, San Diego, CA (US)

(73) Assignee: Ferring B.V., Hoofddorp (NL)

(*) Notice: Subject to any disclaimer, the term of this patent is extended or adjusted under 35 U.S.C. 154(b) by 37 days.

This patent is subject to a terminal disclaimer.

(21) Appl. No.: 13/409,976

(22) Filed: Mar. 1, 2012

(65) Prior Publication Data

US 2012/0196808 A1     Aug. 2, 2012

Related U.S. Application Data

(63) Continuation of application No. 11/659,215, filed as application No. PCT/US2005/027772 on Aug. 3, 2005, now Pat. No. 8,148,319.

(60) Provisional application No. 60/600,377, filed on Aug. 11, 2004.

(30) Foreign Application Priority Data

Aug. 11, 2004   (EP) .................................. 04019029

(51) Int. Cl.
    *A61K 38/00*    (2006.01)
    *C07K 7/16*     (2006.01)

(52) U.S. Cl.
    USPC .......................... 514/15.6; 514/20.8; 530/321

(58) Field of Classification Search
    None
    See application file for complete search history.

(56) References Cited

U.S. PATENT DOCUMENTS

| | | | |
|---|---|---|---|
| 3,352,843 A | 11/1967 | Roger et al. | |
| 4,483,794 A | 11/1984 | Barth et al. | |
| 4,829,051 A | 5/1989 | Cort et al. | |
| 5,459,236 A | 10/1995 | Aurell et al. | |
| 5,516,795 A | 5/1996 | Dellaria et al. | |
| 6,262,021 B1 | 7/2001 | Uvnäs et al. | |
| 6,852,697 B1 | 2/2005 | Mathison et al. | |
| 8,148,349 B2 | 4/2012 | Wisniewski et al. | |
| 8,222,202 B2 * | 7/2012 | Laporte et al. | 514/1.5 |
| 2003/0109670 A1 * | 6/2003 | Olivera et al. | 530/324 |
| 2004/0009550 A1 | 1/2004 | Moll et al. | |
| 2004/0229798 A1 | 11/2004 | Landry et al. | |
| 2009/0275522 A1 * | 11/2009 | Wisniewski et al. | 514/15 |

FOREIGN PATENT DOCUMENTS

| | | |
|---|---|---|
| CZ | CS235151 B1 | 2/1987 |
| CZ | CS242062 B1 | 2/1988 |
| EP | 1027067 A1 | 8/2000 |
| EP | 1406649 A1 | 4/2004 |
| GB | 1 076 984 | 7/1967 |
| RU | 2063979 C1 | 7/1996 |
| RU | 2342949 C1 | 1/2009 |
| WO | WO8801163 A1 | 2/1988 |
| WO | WO8903393 A1 | 4/1989 |
| WO | WO9913092 A1 | 9/1991 |
| WO | WO9946283 A1 | 9/1999 |
| WO | WO02064740 A2 | 8/2002 |
| WO | WO03082334 A1 | 10/2003 |
| WO | WO03099862 A3 | 3/2004 |
| WO | WO2004030524 A3 | 6/2004 |
| WO | WO 2006/020491 * | 2/2006 |

OTHER PUBLICATIONS

Chen, "Vasopressin: New Uses in Critical Care." Southwestern Internal Medicine Conference, vol. 324, No. 3, 2002, pp. 146-154.
Derwent Abstract—XP-002312063, AN 2003-812511, Abstract of AU20030220919 (based on WO0208234), (1 pg.) (2003).
Jolly et al., "Terlipression Infusion in /Catecholamine-resistant shock," Anaesth. Intensive Care, col. 31, 2003, pp. 560-564.
Lauzier et al., "Vasopressin in the treatment of septic shock," Reanimation, vol. 13, 2004, pp. 147-153 (Abstract).
Moureau et al., "Comparison of the effect of terlipression and albumin on arterial blood volume in patients with cirrhosis and tense ascites treated by paracentesis: a radomised pilot study" Gut. vol. 50, 2002, pp. 90-94.
Morelli et al., "Effect of terlipressin on systemic and regional haemodynamis in catecholamine-treated hyperkinetic septic shock" Intensive Care Med., vol. 30, 2004, pp. 597-604.
O'Brien et al., "Terlipression for nonrepinephrine-resistant septic shock," The Lancet., vol. 459, 2002, pp. 1209-1210.
Reid, "Role of Vasopression deficiency in the vasodilation of septic shock," Circulation, vol. 95, 1997, pp. 1108-1110.
Terrillon et al., "Synthesis and Characterization of Fluorescent Antagonists and Agonist for Human Oxytocin Vasopression V1a Receptors" J. Med. Chem., vol. 45, 2002. pp. 2579-2588.

(Continued)

*Primary Examiner* — Karlheinz R Skowronek
*Assistant Examiner* — Roy Teller
(74) *Attorney, Agent, or Firm* — Fish & Richardson P.C.

(57) ABSTRACT

The present application relates to novel compounds, pharmaceutical compositions comprising the same, use of said compounds for the manufacture of a medicament for treatment of inter alia shock conditions as well as to a method for treatment of said conditions, wherein said compounds are administered. The compounds are represented by the general formula (I), as further defined in the specification.

(I)

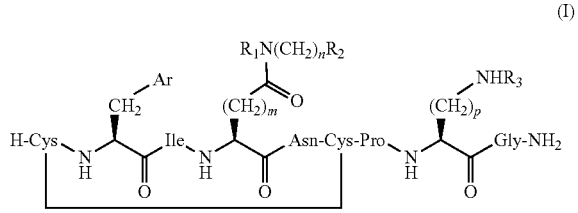

30 Claims, No Drawings

(56) References Cited

OTHER PUBLICATIONS

Wisniewski et al., "The efficient synthesis of FMOC-1-homoglutamine" Oppi Briefs, vol. 29, No. 3, 1997, pp. 338-341.

Walter, E.; "Therapie des hepatorenalen Syndroms"; Praxis, Schweizerische Rundschau Fur Medizin-Inhalt & Zusammenfassungen, vol. 86, No. 4, 1997, Retrieved from the Internet on Jan. 10, 2008 URL:http://www.oraxis.ch/content/1997/04 1997.html> (English Abstracts included).

Dohler, K. D. et al.; "Wirkmechanismen der vasokonstriktiven Therapie der Osophagusvarizenblutung"; Zeitschrift Fur Gastroenterologie, vol. 41, 2003, pp. 1001-1016 (English abstract).

* cited by examiner

PEPTIDIC VASOPRESSIN RECEPTOR AGONISTS

This application is a continuation of U.S. application Ser. No. 11/659,215 filed Feb. 2, 2007, which is pending, which is the national phase of PCT Appl. PCT/US2005/027772 filed Aug. 3, 2005, which claims the benefit of U.S. Prov. Appl. No. 60/600,377, filed Aug. 11, 2004, and European Appl. No. 04019029.0 filed Aug. 11, 2004. Each these prior applications is hereby incorporated by reference in its entirety.

FIELD OF THE INVENTION

The present invention relates to novel compounds, pharmaceutical compositions comprising the same, use of said compounds for the manufacture of a medicament for treatment of inter alia shock conditions as well as to a method for treatment of said conditions, wherein said compounds are administered.

BACKGROUND

Peptidic vasopressin V1a receptor agonists, such as terlipressin, have recently (see e.g. O'Brian et al., Lancet 359 (9313):1209-10, Jun. 4, 2002) received increased attention for clinical use in treatment of critical care diseases and conditions, including shock of hypovolemic (e.g. hemorrhagic) or vasodilatory (e.g. septic) origin, bleeding esophageal varices (BEV), hepatorenal syndrome (HRS), cardiopulmonary resuscitation and anesthesia-induced hypotension. They have also been shown to have clinical use in the treatment of orthostatic hypotension, paracentesis-induced circulatory dysfunction, intra-operative blood loss and blood loss associated with burn débridement and epistaxis, and for treatment of various ocular diseases by increasing lacrimation/tear formation.

In treating critical care conditions it is highly desirable to control the arterial blood pressure, and the drug used is typically administered intravenously. Continuous intravenous drug infusion at increasing or decreasing rates is a practical means of providing the desired degree of control. The attainment of so-called "steady state" plasma concentrations of drug depends on the elimination half life of the drug infused. It is generally recognised that steady state plasma concentration is achieved after a period of time equivalent to three times the elimination half life of the drug. To be practical in a clinical setting the desired arterial blood pressure at the steady state should be attained in about two hours, preferably in one hour or less. V1a agonists with an elimination half life longer than 1 hour are therefore usually not considered useful for critical care treatment.

A disadvantage of terlipressin in many critical care situations is its long duration of action, which makes it difficult to titrate its effect as the disease state changes. The efficacy of terlipressin at the human V1a (hV1a) receptor also needs to be improved e.g. to allow lower dosages in general.

Also the compound known as F180 (cf. example 3 in U.S. Pat. No. 5,459,236) has an inconveniently long duration of action to be considered for the treatment of most critical care conditions.

Non-specific receptor agonist activity is the main disadvantage of other existing compounds, e.g. [Phe2,Orn8]OT (cf. example if in U.S. Pat. No. 3,352,843) and arginine-vasopressin (AVP). Activity at related receptors such as V1b, V2 and oxytocin (OT) receptors may potentially generate undesirable side effects and safety concerns. As an example, V2 receptor activation may induce antidiuresis (cf. desmopressin), release of coagulation/thrombolysis factors, and induce vasodilation/hypotension with reflex tachycardia. The latter side effect may also be induced by OT receptor agonist activity.

It is an objective of the present invention to provide compounds that are especially useful in the treatment of critical care conditions.

DISCLOSURE OF THE INVENTION

The present invention relates to compounds represented by the general formula (I) (SEQ ID NO: 53):

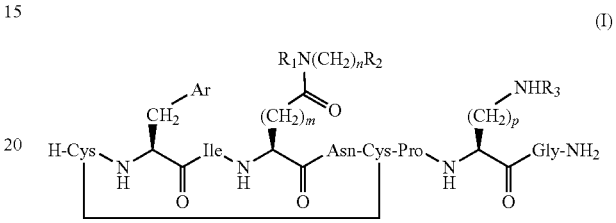

(I)

wherein:
Ar is an aryl, group selected from aromatic carbocyclic ring systems, five- or six-membered heteroaromatic ring systems and bicyclic heteroaromatic ring systems;
m is selected from 1, 2 and 3;
n is selected from 0, 1, 2, 3 and 4;
p is selected from 2, 3 and 4;
$R_1$, $R_2$ and $R_3$ are independently selected from H, OH, alkyl, O-alkyl and OC(O)-alkyl;
alkyl is selected from $O_{1-6}$ straight and $C_{4-8}$ branched chain alkyl and optionally has at least one hydroxyl substituent;
and when n=0, $R_1$ and $R_2$ optionally together form a nitrogen containing ring structure comprising from 2 to 5 carbon atoms;
with the proviso that when Ar is phenyl (amino acid no. 2 is Phe), m=2, n=0 and $R_1$=$R_2$=H (amino acid no. 4 is Gln) $R_3$ is not H when p is 3 or 4; and
solvates and pharmaceutically acceptable salts thereof.
Amino acid no. 8 is Orn when $R_3$=H and p=3, and Lys when $R_3$=H and p=4.
For the purposes of the present invention, the following terminology is used.
Aromatic carbocyclic ring systems includes phenyl and naphthyl.
A five-membered heteroaromatic ring system is a monocyclic aromatic ring system having five ring atoms, wherein 1, 2 or 3 ring atoms are independently selected from N, O and S. Preferred such ring systems are selected form a group consisting of thienyl, furyl, pyrrolyl, imidazolyl, thiazolyl, oxazolyl, pyrazolyl, isothiazolyl, isoxazolyl and tetrazolyl.
A six-membered heteroaromatic ring system is a monocyclic aromatic ring system having six ring atoms, wherein 1, 2 or 3 ring atoms are independently selected from N, O and S. It is preferably selected from a group consisting of pyridyl, pyrazinyl, pyrimidinyl, triazinyl and pyridazinyl.
A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring; connected by a ring fusion, said bicyclic heteroaromatic ring system comprising 8 to 12 ring atoms, wherein 1, 2 or 3 of the ring atoms are independently selected from N, O and S. It is preferably selected from a group consisting of indole, quinoline, tetrahydroquinoline, isoquinoline, tetrahydroisoquinoline, 1,4-benzodioxan, coumarin, benzofuran, 1,2-benzisoxazole, benzothiophene, benzoxazole, benzthiazole, benzimidazole, benztriazole, pyrolizidine and quinolizidine.

A heterocyclyl or heterocyclic moiety is a saturated or partially saturated ring system having 3 to 7 ring atoms, wherein 1, 2 or 3 ring atoms are independently selected from N, O and S. Heterocyclyl moieties are preferably selected from a group consisting of aziridine, oxirane, thiirane, azetidine, oxetane, thietane, pyrrolidine, pyrroline, imidazolidine, pyrazolidine, dioxolane, tetrahydrofuranyl, piperidine, piperazine, morpholine, tetrahydropyranyl, 1,4-dioxanyl, homopiperidinyl, homopiperazinyl and hexamethylene oxide.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, toluenesulphonic acid and naphtalenesulphonic acid.

Ar is preferably selected from phenyl, 2- or 3-thienyl, 2- or 3-furyl, 2-, 3- or 4-pyridyl and 2-, 4- or 5-thiazolyl. It is particularly preferred that $R_1$ is H.

In preferred embodiments p is 2 or 3.

It is preferred to select $R_2$ from H, OH, $CH_3$, $CH_2CH_3$, $CH(CH_3)_2$, $CH(CH_2OH)_2$, $CH(OH)CH_3$ (both enantiomers), $OCH_3$ and $OCH_2CH_2OH$.

Moreover, it is preferred to select $R_3$ from H, methyl, ethyl, n-propyl, i-propyl and i-amyl.

In the most preferred embodiment, said compound having the formula (I) is selected from a group consisting of (SEQ ID NOs: 1-7, respectively, in order of appearance):

(1) H-Cys-Phe-Ile-Hgn-Asn-Cys-Pro-Orn(i-Pr)-Gly-NH$_2$ (2) H-Cys-Phe-Ile-Asn((CH$_2$)$_3$OH)-Asn-Cys-Pro-Orn-Gly-NH$_2$ (3) H-Cys-Phe-Ile-Asn-Asn-Cys-Pro-Dbu-Gly-NH$_2$ (4) H-Cys-Phe-Ile-Asn(CH$_2$CH$_3$)-Asn-Cys-Pro-Dbu-Gly-NH$_2$ (5) H-Cys-Phe-Ile-Gln-Asn-Cys-Pro-Orn(i-Pr)-Gly-NH$_2$ and (6) H-Cys-Phe-Ile-Gln-Asn-Cys-Pro-Orn(CH$_2$CH$_3$)-Gly-NH$_2$.

(7) H-Cys-Phe-Ile-Asn(CH$_3$)$_2$-Asn-Cys-Pro-Orn-Gly-NH$_2$

The number in parenthesis denotes the compound as referred to in the following.

Furthermore the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, 3$^{rd}$ Ed., American Pharmaceutical Association, USA and Pharmaceutical Press UK, 2000.

The present pharmaceutical composition is most preferably adapted for parenteral administration. It may comprise a sterile aqueous preparation of the compounds of the invention preferably isotonic with the blood of the recipient. This aqueous preparation may be formulated according to known methods using suitable dispersing or wetting agents and suspending agents. The injectable aqueous formulation Remestyp® (terlipressin) is exemplary of a suitable pharmaceutical formulation. The preparation may also be a sterile injectable solution or suspension in a diluent or solvent, for example as a solution in 1,3-butane diol. Water, Ringer's solution, and isotonic sodium chloride solution are exemplary acceptable diluents. Sterile, fixed oils may be employed as a solvent or suspending medium. Bland fixed oils, including synthetic mono or di-glycerides, and fatty acids, such as oleic acid, may also be used.

In addition, the present invention relates to use of a compound as outlined above for the manufacture of a medicament for treatment of shock of hypovolemic or vasodilatory origin, BEV, HRS, cardiopulmonary resuscitation, anesthesia-induced hypotension, orthostatic hypotension, paracentesis-induced circulatory dysfunction, intraoperative blood loss or blood loss associated with burn débridement and epistaxis, and for treatment of various ocular diseases by increasing lacrimation/tear formation.

In another embodiment the invention relates to a method for treatment of shock of hypovolemic or vasodilatory origin, BEV, HRS, cardiopulmonary resuscitation, anesthesia-induced hypotension, orthostatic hypotension, paracentesis-induced circulatory dysfunction, intraoperative blood loss or blood loss associated with burn débridement and epistaxis, and of various ocular diseases by increasing lacrimation/tear formation, wherein said method comprises administering to an animal, including human, patient of a therapeutically effective amount of a compound as outlined above.

The typical dosage of the compounds according to the present invention varies within a wide range and will depend on various factors such as the individual needs of each patient and the route of administration. The dosage administered by infusion is generally within the range of 0.01-200 µg/kg body weight per hour. A physician of ordinary skill in the art will be able to optimise the dosage to the situation at hand.

| | |
|---|---|
| Abu | 2-aminobutyric acid |
| Boc | tert-butoxycarbonyl |
| BOP | benzotriazol-1-yloxy trisdimethylamino-phosphonium hexafluorophosphate |
| Dbu | 2,4-diaminobutyric acid |
| DCC | N,N'-dicyclohexylcarbodiimide |
| DCHA | dicyclohexylamine |
| DCM | dichloromethane |
| DIAD | diisopropyl diazodicarboxylate |
| DIC | N,N'-diisopropylcarbodiimide |
| DIEA | N,N-diisopropyl-N-ethylamine |
| DMF | N,N-dimethylformamide |
| Fm | 9-fluorenylmethyl |
| Fmoc | 9-fluorenylmethoxycarbonyl |
| Hgn | homoglutamine |
| Hmp | 2-hydroxy-3-mercaptopropionic acid |
| HOBt | 1-hydroxybenzotriazole |
| HPLC | high performance liquid chromatography |
| i | iso |
| Mmt | 4-methoxytrityl |
| Mob | p-methoxybenzyl |
| MS | mass spectrometry |
| Orn | ornithine |
| Ph | phenyl |
| Pr | propyl |
| PyBOP | benzotriazol-1-yloxy trispyrrolidine-phosphonium hexafluorophosphate |
| o-NBS-Cl | 2-nitrobenzenesulfonyl chloride |
| OT | oxytocin |
| Rt | retention time |
| TFA | trifluoroacetic acid |
| TIS | triisopropylsilane |
| TMOF | trimethylorthoformate |
| TPP | triphenylphosphine |
| Trt | trityl |
| VT | vasotocin, [Ile$^3$] vasopressin |

Unless otherwise specified L-amino acids were used, and conventional amino acid terminology is adhered to.

EXPERIMENTAL

Synthesis

Amino acid derivatives and resins were purchased from commercial providers (Novabiochem, Bachem Peptide International and PepTech Corporation). Fmoc-Hgn-OH was synthesised according to literature (Wisniewski, K., Kolodziejczyk, A. S. *Org. Prep. Proced. Int.* 1997, 29, 338-341). Other chemicals and solvents were provided from Sigma-Aldrich, Fisher Scientific and VWR.

The compounds herein were synthesised by standard methods in solid phase peptide chemistry utilising both Fmoc and Boc methodology. Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis. A Practical Guide*, Marcel Dekker, New York, Basel, 2000;

Stewart, J. M., Young, J. D. *Solid Phase Synthesis*, Pierce Chemical Company, 1984;

Bisello, et al., *J. Biol. Chem.* 1998, 273, 22498-22505; and Merrifield, *J. Am. Chem. Soc.* 1963, 85, 2149-2154.

Purity of the synthesized peptide may be determined by analytical reversed phase HPLC. Structural integrity of the peptides may be confirmed using amino acid analysis and electrospray mass spectrometry.

The peptides synthesised by Fmoc methodology were cleaved with a TFA/TIS/H$_2$O 96/2/2 (v/v/v) solution, and cleavage in Boc methodology was accomplished with 90% HF/10% anisole (v/v) solution. Disulfide bridge (ring) formation was achieved by oxidation of linear peptides dissolved in 10% TFA (aq) with iodine. Peptides were purified by preparative HPLC in triethylammonium phosphate buffers (aq). The compounds were finally converted to acetate salts using conventional HPLC methodology. The fractions with a purity exceeding 97% were pooled and lyophilised.

Synthesis of peptides with alkylated side chain in position no. 8:

The peptides were assembled with Fmoc methodology. The diamino acid residue in position no. 8 was introduced with an acid labile (i.e. removable with a solution containing 1-2% TFA) protecting group, such as methoxytrityl (Mmt; see Barlos, K. et al. in *Peptides* 1992, Schneider, C. H., Eberle, A. N., Eds., ESCOM Science Publishers B.V., 1993, pp 283-284). Resin bound peptide was treated with a DCM/TIS/TFA 93/5/2 (v/v/v) solution for the Mmt group removal. Reductive alkylation with acetone/NaBH(OAc)$_3$ provided the N-isopropyl peptide.

To avoid undesirable N,N-dialkylation in reductive alkylation in the above procedure, which may occur when straight chain alkyl aldehydes are used, an alternative was developed, wherein after the Mmt removal the amino group was first derivatised with 2-nitrobenzenesulfonyl chloride (o-NBS-Cl; see Fukuyama, T.; Jow, C.-K.; Cheung, M. *Tetrahedron Lett.* 1995, 36, 6373-6374). The resulting sulphonamide was then alkylated with an appropriate alcohol under conventional Mitsunobu reaction conditions, typically utilising TPP/DIAD in 1,2-dimethoxyethane (Mitsunobu, O. *Synthesis* 1981, 1-28). The o-NBS-Cl group was subsequently removed with 5% potassium thiophenolate in DMF, after which the peptide was cleaved from the resin.

Synthesis of peptides with N-alkylated side chain in position no. 4:

The peptides were assembled with Boc methodology. The residue in position no. 4 was introduced in the sequence as Boc-Asp(OFm)-OH. After complete peptide assembly the side chain protection was removed with 30% piperidine in DMF. The resulting free carboxylic group was converted to the desired amide by coupling with an appropriate amine mediated by PyBOP or BOP/DIEA. The N-terminal Boc group was then removed, followed by HF cleavage, cyclisation and purification by HPLC.

Table 1 lists the compounds prepared by the above procedure. R$_1$ is H for all compounds except no. 7, where R$_1$ is CH$_3$. An asterisk "*" marks the most preferred embodiments.

TABLE 1

Compounds prepared with the formula (I)

| Substituent | | | | | | Denoted SEQ ID NO |
|---|---|---|---|---|---|---|
| Ar | m | n | R$_2$ | p | R$_3$ | |
| Ph | 2 | 0 | H | 2 | H | 8 |
| Ph | 3 | 0 | H | 3 | H | 9 |
| Ph | 2 | 0 | OCH$_3$ | 3 | H | 10 |

TABLE 1-continued

Compounds prepared with the formula (I)

| Substituent | | | | | Denoted SEQ ID |
|---|---|---|---|---|---|
| Ar | m | n | $R_2$ | p | $R_3$ | NO |
| Ph | 3 | 0 | H | 2 | H | 11 |
| 4-pyridyl | 2 | 0 | H | 2 | H | 12 |
| 4-thiazolyl | 2 | 0 | H | 2 | H | 13 |
| 2-thienyl | 2 | 0 | H | 2 | H | 14 |
| 3-thienyl | 2 | 0 | H | 2 | H | 15 |
| Ph | 2 | 0 | OH | 3 | H | 16 |
| 2-pyridyl | 2 | 0 | H | 2 | H | 17 |
| 3-pyridyl | 2 | 0 | H | 2 | H | 18 |
| Ph | 2 | 0 | $CH_3$ | 3 | H | 19 |
| Ph | 2 | 1 | $CH_3$ | 3 | H | 20 |
| Ph | 2 | 1 | $CH(CH_3)_2$ | 3 | H | 21 |
| Ph | 3 | 0 | H | 3 | $CH(CH_3)_2$ | 1* |
| Ph | 3 | 0 | H | 2 | $CH(CH_3)_2$ | 22 |
| Ph | 1 | 2 | OH | 3 | H | 23 |
| Ph | 1 | 0 | OH | 3 | H | 24 |
| 2-furyl | 2 | 0 | H | 3 | H | 25 |
| Ph | 1 | 3 | OH | 3 | H | 2* |
| 2-furyl | 2 | 0 | H | 2 | H | 26 |
| Ph | 1 | 0 | $CH(CH_2OH)_2$ | 3 | H | 27 |
| Ph | 1 | 1 | $CH(OH)CH_3$ | 3 | H | 28 |
| Ph | 1 | 2 | $OCH_2CH_2OH$ | 3 | H | 29 |
| Ph | 1 | 0 | H | 3 | H | 30 |
| Ph | 1 | 0 | H | 2 | H | 3* |
| Ph | 1 | 0 | $CH_3$ | 2 | H | 31 |
| Ph | 1 | 1 | $CH_3$ | 2 | H | 4* |
| 2-furyl | 2 | 0 | H | 3 | H | 32 |
| 2-thienyl | 1 | 0 | H | 3 | H | 33 |
| Ph | 2 | 0 | H | 3 | $CH(CH_3)_2$ | 5* |
| 2-thienyl | 2 | 0 | H | 3 | $CH(CH_3)_2$ | 34 |
| 3-thienyl | 1 | 0 | H | 3 | H | 35 |
| 2-thienyl | 1 | 0 | H | 2 | H | 36 |
| 3-thienyl | 1 | 0 | H | 2 | H | 37 |
| 2-furyl | 1 | 0 | H | 3 | H | 38 |
| Ph | 2 | 0 | H | 3 | $CH_3$ | 39 |
| Ph | 2 | 0 | H | 3 | $CH_2CH_2CH_3$ | 40 |
| Ph | 1 | 0 | H | 3 | $CH(CH_3)_2$ | 41 |
| 2-furyl | 1 | 0 | H | 3 | $CH(CH_3)_2$ | 42 |
| 2-thienyl | 1 | 0 | H | 3 | $CH(CH_3)_2$ | 43 |
| 2-furyl | 1 | 0 | H | 2 | H | 44 |
| Ph | 2 | 0 | H | 3 | $CH_2CH_3$ | 6* |
| Ph | 2 | 0 | H | 3 | $(CH_2)_2CH(CH_3)_2$ | 45 |
| Ph | 1 | 0 | H | 3 | $CH_3$ | 46 |
| Ph | 1 | 0 | H | 3 | $CH_2CH_3$ | 47 |
| Ph | 1 | 0 | $CH_3$ | 3 | H | 7* |
| Ph | 1 | 1 | $CH_3$ | 3 | H | 48 |
| Ph | 1 | 0 | $CH_3$ | 3 | H | 49 |
| Ph | 1 | 0 | H | 3 | $CH_2CH_2CH_3$ | 50 |

The following detailed examples are provided to further illustrate the synthesis:

Compound 1; [Phe², Hgn⁴, Orn (i-Pr)⁸]VT:

The amino acid derivatives used were Boc-Cys(Trt)-OH, Fmoc-Phe-OH, Fmoc-11e-OH, Fmoc-Hgn-OH, Fmoc-Asn (Trt)-OH, Fmoc-Cys(Trt)-OH, Fmoc-Pro-OH, Fmoc-Orn (Mmt)-OH and Fmoc-Gly-OH. Fmoc-Hgn-OH was synthesised as mentioned above. Analytical HPLC was performed on a Waters 600 Liquid Chromatograph using a Vydac C18, 5µ 4.6×250 mm, column at a flow rate of 2 ml/min. Preparative HPLC was performed on a Waters 2000 Liquid Chromatograph using a Prepak 47×300 mm cartridge at a flow rate of 100 ml/min. Final compound analysis was performed on a 1100 Agilent Liquid Chromatograph using a Vydac C18, 5µ 2.1×250 mm, column at a flow rate of 0.3 ml/min. Mass spectra were recorded on a Finnigan MAT spectrometer.

The fully protected peptide resin was synthesised on an Applied Biosystems 9050 Peptide Synthesiser starting from 2 g (0.5 mmol) of Tentagel-S-RAM resin (Peptides International). DIC/HOBt mediated single couplings with a 4-fold excess of amino acid derivatives were performed. The Fmoc group was removed with 20% piperidine in DMF. Upon completion of the automated synthesis, the resin was transferred into a manual synthesis vessel and was treated with DCM/TIS/TFA 93/5/2 (v/v/v) solution (30 ml) for 2×1.5 hours for removal of the Mmt group. The resin was thoroughly washed with DCM and was subsequently suspended in 15 ml of 1,2-dichloroetehane/TMOF 1:1 (v/v). 0.2 ml of acetone was then added followed by 0.6 g of NaBH(OAc)₃. The suspension was shaken overnight and the resin was washed with methanol, DMF and DCM and dried in vacuo. The resin was then treated with 30 ml of the TFA/TIS/H₂O 96/2/2 (v/v/v) solution for 1.5 hours and filtered off. The filtrate was evaporated and the crude linear peptide was precipitated with diethyl ether. The precipitate was immediately dissolved in 500 ml of 10% TFA (aq), and the peptide was oxidised by adding 0.1 M I₂ in methanol to the magnetically stirred solution until yellow color persisted. Excess of iodine was reduced with ascorbic acid. The reaction mixture was then cooled with crushed ice and pH was adjusted to about 5 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, and the resulting solution was diluted with 2 volumes of water. The solution was reloaded onto the column which was then washed with 2 l of 0.1 M ammonium acetate (aq) and equilibrated with 2% acetic acid (aq). The compound was eluted with a fast (3%/min) gradient of acetonitrile. The fractions containing the desired product were pooled and lyophilised. 168 mg (~30% yield) of white amorphous powder was obtained. HPLC: Rt=8.5 min, gradient: 20→40% B over 20 min, t=40° C., solvent A 0.01% TFA (aq), solvent B 70% CH₃CN, 0.01% TFA (aq); Purity: 98.8%; MS (M+H⁺): expected 1048.5, observed 1048.5.

Compound 4; [Phe², Asn (Et)⁴, Dbu⁸]VT:

The amino acid derivatives used were Boc-Cys(Mob)-OH, Boc-Phe-OH, Boc-Ile—OH, Boc-Asp(OFm)—OH, Boc-Asn-OH, Boc-Pro-OH, Boc-Dbu(benzyloxycarbonyl)-OH DOHA salt and Boc-Gly-OH, all purchased from Novabiochem and Bachem. HPLC and MS operations were performed as in the synthesis of compound 1.

The fully protected peptide resin was manually synthesised starting from 0.6 g (0.4 mmol) of 4-methylbenzhydrylamine resin (Novabiochem). DCC, PyBOP or DIC/HOBt mediated single couplings with 2.5-fold excess of amino acid derivatives were employed. The Boc group was removed with 50% TFA in DCM containing 1% of m-cresol. Upon completion of the synthesis, the 9-fluorenylmethyl ester was removed from the β-carboxylic group of aspartic acid by treatment with 30% piperidine in DMF for 2×30 min. The resin was washed with 1 M HOBt in DMF solution for 30 min and then twice with DMF only. The free carboxylic group was amidated by overnight treatment with 2 mmol of ethylamine/PyBOP/DIEA in DMF. The finished resin was washed with methanol, DMF and DCM and dried in vacuo. The peptide was cleaved from the resin by using 30 ml of anhydrous HF containing 3 ml of anisole at 0° C. for 90 minutes. The HF was evaporated off, and the crude linear peptide was washed with diethyl ether. The peptide was immediately dissolved in 200 ml of 25% acetonitrile/10% TFA (aq) and oxidised as described supra. The resulting mixture was loaded directly onto an HPLC column and purified using triethylammonium phosphate buffer at pH 2.3. The subsequent purification steps were identical to the procedure for compound 1. 41 mg (~10% yield) of white amorphous powder was obtained. HPLC: Rt=10.0 min, gradient: 20.40% B over 20 min, t=40° C., solvent A 0.01% TFA (aq), solvent B 70% $CH_3CN$, 0.01% TFA (aq); Purity: 100%; MS (M+H$^+$): expected 992.5, observed 992.2.

The other compounds were prepared by analogous variation of these synthetic procedures.

EXPERIMENTAL

Biological Testing

In vitro receptor assays:

Agonist activity of compounds on the hV1a receptor was determined in a transcriptional reporter assay by transiently transfecting a hV1a receptor expression DNA into HEK-293 cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 hours, followed by lysis of cells, determination of luciferace activity, and determination of compound efficacies and $EC_{50}$ values through non-linear regression. Arginine-vasopressin (AVP) was used as an internal control in each experiment, and compounds were tested in at least three independent experiments. To determine selectivity, compounds were tested in luciferase-based transcriptional reporter assays expressing the human oxytocin (hOT) receptor. Assays for other receptors (hV2, hV1b, rat V1a and rat V2) were also conducted.

For further comparative purposes, other reference compounds used were [Phe2,Orn8]OT, terlipressin and F180.

The structure of [Phe2,Orn8]OT is (SEQ ID NO: 51):

H-Cys-Phe-Ile-Gln-Asn-Cys-Pro-Orn-Gly-NH$_2$

The structure of F180 is (SEQ ID NO: 52):

Hmp-Phe-Ile-Hgn-Asn-Cys-Pro-Dbu(Abu)-Gly-NH$_2$
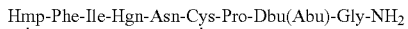

The results of the in vitro assays are depicted in table 2 infra. The $EC_{50}$ value given is the geometric mean expressed in nanomol/L (nM). Selectivity values are given as $EC_{50}$ ratios.

In vivo pharmacological tests:

The compounds were tested in vivo for duration of action related to a standard dose of AVP. Blood pressure tests were carried out on anaesthetised Sprague-Dawley male rats (weighing 270-300 g) with catheterised jugular vein and carotid artery. The catheterised carotid artery was used to continuously monitor blood pressure and the jugular vein was used for administration of the compounds tested. Rats received intravenous injections of dibenamine prior to dosing to enhance their responsiveness to V1a receptor agonists (cf. Dekanski, J., *Br. J. Pharmacol.* 1952, 7, 567-572). The dosing procedure consisted of one intravenous injection of physiological saline followed by two consecutive injections of a standard dose of AVP (0.1 nmol/kg, $\approx ED_{70}$), and three to five increasing doses of a given compound selected to give at least a response comparable to the standard dose of AVP. Dosing intervals were set as time for the blood pressure to decrease to a stable baseline.

Determination of duration of action was based on the decay rate of diastolic arterial blood pressure transient increase. Specifically, for an exponential decay of plasma concentration, it can be shown that, if the response is measured beyond the distribution phase, the rate of decay near the $EC_{50}$ is linear and inversely proportional to the elimination half-life (Rowland, M. and Tozer, T. in *"Clinical Pharmacokinetics, Concepts and Applications"*, 3$^{rd}$ ed., Lippincott Williams & Wilkins, Philadelphia, 1995).

To measure the response decay rate for a given compound, a dose was selected that gave an amplitude of response as similar as possible to the amplitude of response to the second injection of the standard dose of AVP. To normalise for inter-individual variation in V1a-responsiveness, the duration of action was expressed as the ratio of decay rate for this reference AVP response to the decay rate for the equieffective dose of compound for each rat tested. The results obtained for the compounds tested are set forth in table 2.

TABLE 2

Results of biological testing

| Compound tested | $EC_{50}$ hV1a receptor | in vivo duration relative to AVP | selectivity hOT/hV1a |
|---|---|---|---|
| 8 | 0.50 | – | 11 |
| 9 | 0.68 | 1.5 | + |
| 10 | 1.15 | 2.3 | 11 |
| 11 | 2.96 | 1.9 | + |
| 12 | 24.96 | – | + |
| 13 | 18.77 | – | + |
| 14 | 0.54 | – | 75 |
| 15 | 0.61 | 2.2 | 43 |
| 16 | 11.88 | – | + |
| 17 | 30.29 | – | + |
| 18 | 29.85 | – | + |
| 19 | 5.99 | 1.6 | + |
| 20 | 39.28 | – | + |
| 21 | 20.66 | – | + |
| 1* | 2.02 | 1.7 | + |
| 22 | 18.13 | – | + |
| 23 | 7.97 | – | + |
| 24 | 4.09 | – | + |
| 25 | 1.40 | 2.0 | 23 |
| 2* | 1.18 | 1.7 | + |
| 26 | 2.24 | 2.0 | 28 |
| 27 | 16.21 | – | + |
| 28 | 5.17 | – | + |
| 29 | 4.77 | – | + |
| 30 | 1.45 | 1.7 | + |
| 3* | 1.47 | 1.7 | + |
| 31 | 3.91 | – | + |
| 4* | 2.36 | 1.8 | + |
| 32 | 2.64 | 2.1 | 35 |
| 33 | 14.61 | – | + |
| 5* | 0.25 | 1.9 | 117 |
| 34 | 0.73 | 2.0 | 72 |
| 35 | 7.30 | – | + |
| 36 | 11.54 | – | + |
| 37 | 7.45 | – | + |
| 38 | 10.11 | – | + |
| 39 | 0.21 | 1.9 | 178 |
| 40 | 0.27 | 2.0 | 88 |
| 41 | 0.98 | 2.6 | 53 |
| 42 | 6.25 | – | + |
| 43 | 13.71 | – | + |
| 44 | 14.48 | – | + |
| 6* | 0.29 | 1.9 | 86 |
| 45 | 1.65 | – | 18 |

TABLE 2-continued

Results of biological testing

| Compound tested | EC$_{50}$ hV1a receptor | in vivo duration relative to AVP | selectivity hOT/hV1a |
|---|---|---|---|
| 46 | 2.41 | 2.1 | + |
| 47 | 0.99 | 1.6 | + |
| 7* | 2.84 | − | + |
| 48 | 5.70 | − | + |
| 49 | 3.58 | − | + |
| 50 | 1.52 | 2.4 | 43 |
| [Phe2, Orn8]OT | 0.15 | 1.9 | 60 |
| terlipressin | 82.08 | 9.1 | + |
| AVP | 0.21 | 0.9 | 108 |
| F180 | 0.56 | 3.8 | + |

− = not tested
+ = selective hV1a receptor agonist; EC$_{50}$ hOT/hV1a ratio not determined due to very low agonist efficacy (<30% compared to AVP) at the hOT receptor All references listed are

```
Cys Phe Ile Asn Asn Cys Pro Xaa Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CH3)
<220> FEATURE:
<221> NAME/KEY: MOD_RES
<222> LOCATION: (8)
<223> OTHER INFORMATION: Dbu

<400> SEQUENCE: 4

Cys Phe Ile Asn Asn Cys Pro Xaa Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Pr)

<400> SEQUENCE: 5

Cys Phe Ile Gln Asn Cys Pro Xaa Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH3)

<400> SEQUENCE: 6

Cys Phe Ile Gln Asn Cys Pro Xaa Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH3)2
<220> FEATURE:
<221> NAME/KEY: MOD_RES
<222> LOCATION: (8)
<223> OTHER INFORMATION: Orn
```

```
<400> SEQUENCE: 7

Cys Phe Ile Asn Asn Cys Pro Xaa Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Dbu

<400> SEQUENCE: 8

Cys Phe Ile Gln Asn Cys Pro Xaa Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Orn

<400> SEQUENCE: 9

Cys Phe Ile Xaa Asn Cys Pro Xaa Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Glu(NHOCH3)
<220> FEATURE:
<221> NAME/KEY: MOD_RES
<222> LOCATION: (8)
<223> OTHER INFORMATION: Orn

<400> SEQUENCE: 10

Cys Phe Ile Glu Asn Cys Pro Xaa Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hgn
```

```
<220> FEATURE:
<221> NAME/KEY: MOD_RES
<222> LOCATION: (8)
<223> OTHER INFORMATION: Dbu

<400> SEQUENCE: 11

Cys Phe Ile Xaa Asn Cys Pro Xaa Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4-Pal
<220> FEATURE:
<221> NAME/KEY: MOD_RES
<222> LOCATION: (8)
<223> OTHER INFORMATION: Dbu

<400> SEQUENCE: 12

Cys Xaa Ile Gln Asn Cys Pro Xaa Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(4-Thz)
<220> FEATURE:
<221> NAME/KEY: MOD_RES
<222> LOCATION: (8)
<223> OTHER INFORMATION: Dbu

<400> SEQUENCE: 13

Cys Ala Ile Gln Asn Cys Pro Xaa Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 14

Cys Xaa Ile Gln Asn Cys Pro Xaa Gly
1               5

<210> SEQ ID NO 15
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 15

Cys Xaa Ile Gln Asn Cys Pro Xaa Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Glu(NHOH)
<220> FEATURE:
<221> NAME/KEY: MOD_RES
<222> LOCATION: (8)
<223> OTHER INFORMATION: Orn

<400> SEQUENCE: 16

Cys Phe Ile Glu Asn Cys Pro Xaa Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 2-Pal
<220> FEATURE:
<221> NAME/KEY: MOD_RES
<222> LOCATION: (8)
<223> OTHER INFORMATION: Dbu

<400> SEQUENCE: 17

Cys Xaa Ile Gln Asn Cys Pro Xaa Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Pal
<220> FEATURE:
<221> NAME/KEY: MOD_RES
<222> LOCATION: (8)
<223> OTHER INFORMATION: Dbu
```

<400> SEQUENCE: 18

Cys Xaa Ile Gln Asn Cys Pro Xaa Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(CH3)
<220> FEATURE:
<221> NAME/KEY: MOD_RES
<222> LOCATION: (8)
<223> OTHER INFORMATION: Orn

<400> SEQUENCE: 19

Cys Phe Ile Gln Asn Cys Pro Xaa Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(CH2CH3)
<220> FEATURE:
<221> NAME/KEY: MOD_RES
<222> LOCATION: (8)
<223> OTHER INFORMATION: Orn

<400> SEQUENCE: 20

Cys Phe Ile Gln Asn Cys Pro Xaa Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Gln(i-Bu)
<220> FEATURE:
<221> NAME/KEY: MOD_RES
<222> LOCATION: (8)
<223> OTHER INFORMATION: Orn

<400> SEQUENCE: 21

Cys Phe Ile Gln Asn Cys Pro Xaa Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic

```
                           peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Dbu(i-Pr)

<400> SEQUENCE: 22

Cys Phe Ile Xaa Asn Cys Pro Xaa Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
                           peptide
<220> FEATURE:
<221> NAME/KEY: MOD_RES
<222> LOCATION: (4)
<223> OTHER INFORMATION: Asn(CH2CH2OH)
<220> FEATURE:
<221> NAME/KEY: MOD_RES
<222> LOCATION: (8)
<223> OTHER INFORMATION: Orn

<400> SEQUENCE: 23

Cys Phe Ile Asn Asn Cys Pro Xaa Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
                           peptide
<220> FEATURE:
<221> NAME/KEY: MOD_RES
<222> LOCATION: (4)
<223> OTHER INFORMATION: Asn(OH)
<220> FEATURE:
<221> NAME/KEY: MOD_RES
<222> LOCATION: (8)
<223> OTHER INFORMATION: Orn

<400> SEQUENCE: 24

Cys Phe Ile Asn Asn Cys Pro Xaa Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
                           peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn

<400> SEQUENCE: 25

Cys Ala Ile Gln Asn Cys Pro Xaa Gly
```

```
<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Dbu

<400> SEQUENCE: 26

Cys Ala Ile Gln Asn Cys Pro Xaa Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asp(CH(CH2OH)2)
<220> FEATURE:
<221> NAME/KEY: MOD_RES
<222> LOCATION: (8)
<223> OTHER INFORMATION: Orn

<400> SEQUENCE: 27

Cys Phe Ile Asp Asn Cys Pro Xaa Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH2CHOHCH3)
<220> FEATURE:
<221> NAME/KEY: MOD_RES
<222> LOCATION: (8)
<223> OTHER INFORMATION: Orn

<400> SEQUENCE: 28

Cys Phe Ile Asn Asn Cys Pro Xaa Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
```

```
<223> OTHER INFORMATION: Asn(CH2CH2OCH2CH2OH)
<220> FEATURE:
<221> NAME/KEY: MOD_RES
<222> LOCATION: (8)
<223> OTHER INFORMATION: Orn

<400> SEQUENCE: 29

Cys Phe Ile Asn Asn Cys Pro Xaa Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 30

Cys Phe Ile Asn Asn Cys Pro Xaa Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Dbu

<400> SEQUENCE: 31

Cys Phe Ile Asn Asn Cys Pro Xaa Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 32

Cys Ala Ile Gln Asn Cys Pro Xaa Gly
1               5

<210> SEQ ID NO 33
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn

<400> SEQUENCE: 33

Cys Xaa Ile Asn Asn Cys Pro Xaa Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 34

Cys Xaa Ile Gln Asn Cys Pro Xaa Gly
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Orn

<400> SEQUENCE: 35

Cys Xaa Ile Asn Asn Cys Pro Xaa Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 36
```

```
Cys Xaa Ile Asn Asn Cys Pro Xaa Gly
1               5
```

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 37

```
Cys Xaa Ile Asn Asn Cys Pro Xaa Gly
1               5
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn

<400> SEQUENCE: 38

```
Cys Ala Ile Asn Asn Cys Pro Xaa Gly
1               5
```

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH3)

<400> SEQUENCE: 39

```
Cys Phe Ile Gln Asn Cys Pro Xaa Gly
1               5
```

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH2CH3)

<400> SEQUENCE: 40

```
Cys Phe Ile Gln Asn Cys Pro Xaa Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Pr)

<400> SEQUENCE: 41

Cys Phe Ile Asn Asn Cys Pro Xaa Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 42

Cys Ala Ile Asn Asn Cys Pro Xaa Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 43

Cys Xaa Ile Asn Asn Cys Pro Xaa Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala(2-Fur)
<220> FEATURE:
```

```
<221> NAME/KEY: MOD_RES
<222> LOCATION: (8)
<223> OTHER INFORMATION: Dbu

<400> SEQUENCE: 44

Cys Ala Ile Asn Asn Cys Pro Xaa Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(i-Am)

<400> SEQUENCE: 45

Cys Phe Ile Gln Asn Cys Pro Xaa Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH3)

<400> SEQUENCE: 46

Cys Phe Ile Asn Asn Cys Pro Xaa Gly
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH3)

<400> SEQUENCE: 47

Cys Phe Ile Asn Asn Cys Pro Xaa Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 48

Cys Phe Ile Asn Asn Cys Pro Xaa Gly
```

```
1               5
```

```
<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Orn

<400> SEQUENCE: 49

Cys Phe Ile Asn Asn Cys Pro Xaa Gly
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn(CH2CH2CH3)

<400> SEQUENCE: 50

Cys Phe Ile Asn Asn Cys Pro Xaa Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Orn

<400> SEQUENCE: 51

Cys Phe Ile Gln Asn Cys Pro Xaa Gly
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Hmp
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
```

```
<223> OTHER INFORMATION: Dbu(Abu)

<400> SEQUENCE: 52

Xaa Phe Ile Xaa Asn Cys Pro Xaa Gly
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<223> OTHER INFORMATION: see specification as filed for detailed
      description of substitutions and preferred
      embodiments

<400> SEQUENCE: 53

Cys Xaa Ile Xaa Asn Cys Pro Xaa Gly
1               5
```

The invention claimed is:

1. A compound having the formula (I) (SEQ ID NO: 53):

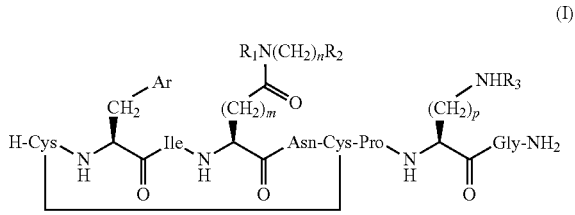

or a pharmaceutically acceptable salt thereof, wherein:
Ar is an aryl group selected from aromatic carbocyclic ring systems, five- or six-membered heteroaromatic ring systems and bicyclic heteroaromatic ring systems;
m is selected from 1, 2 and 3;
n is selected from 0, 1, 2, 3 and 4;
p is selected from 2, 3 and 4;
$R_1$, $R_2$ and $R_3$ are independently selected from H, OH, alkyl, O-alkyl and OC(O)-alkyl;
alkyl is selected from $C_{1-6}$ straight and $C_{4-8}$ branched chain alkyl and optionally has at least one hydroxyl substituent;
and when n=0, $R_1$ and $R_2$ optionally together form a nitrogen containing ring structure comprising from 2 to 5 carbon atoms;
with the proviso that when Ar is phenyl, m=2, n=0, $R_1$=$R_2$=H, and p is 3 or 4, $R_3$ is not H.

2. A compound or pharmaceutically acceptable salt thereof according to claim 1, wherein Ar is selected from phenyl, 2- or 3-thienyl, 2- or 3-furyl, 2-, 3- or 4-pyridyl and 2-, 4- or 5-thiazolyl.

3. A compound or pharmaceutically acceptable salt thereof according to claim 1, wherein $R_1$ is H.

4. A compound or pharmaceutically accutable salt thereof according to claim 1, wherein p is 2 or 3.

5. A compound or pharmaceutically acceptable salt thereof according to claim 1, wherein $R_2$ is selected from H, OH, $CH_3$, $CH_2CH_3$, $CH(CH_3)_2$, $CH(CH_2OH)_2$, $CH(OH)CH_3$, $OCH_3$ and $OCH_2CH_2OH$.

6. A compound or pharmaceutically acceptable salt thereof according to claim 1, wherein $R_3$ is selected from H, methyl, ethyl, n-propyl, i-propyl and i-amyl.

7. A pharmaceutical composition comprising a compound according to claim 1 or a pharmaceutically acceptable salt thereof as an active ingredient and a pharmaceutically acceptable adjuvant, diluent or carrier.

8. A compound or pharmaceutically acceptable salt thereof according to claim 1, wherein Ar is phenyl.

9. A compound or pharmaceutically acceptable salt thereof according to claim 1, wherein m is 1, $R_1$ is H.

10. A compound or pharmaceutically acceptable salt thereof according to claim 9, wherein $R_2$ is H.

11. A compound or pharmaceutically acceptable salt thereof according to claim 9, wherein $R_2$ is OH, methyl, ethyl, i-propyl, $CH(CH_2OH)_2$, $CH(OH)CH_3$, OMe or $OCH_2CH_2OH$.

12. A compound or pharmaceutically acceptable salt thereof according to claim 1, wherein m is 2, $R_1$ is H.

13. A compound or pharmaceutically acceptable salt thereof according to claim 12, wherein $R_2$ is H.

14. A compound or pharmaceutically acceptable salt thereof according to claim 12, wherein $R_2$ is OH, methyl, ethyl, i-propyl, $CH(CH_2OH)_2$, $CH(OH)CH_3$, OMe or $OCH_2CH_2OH$.

15. A compound or pharmaceutically acceptable salt thereof according to claim 1, wherein m is 3, $R_1$ is H.

16. A compound or pharmaceutically acceptable salt thereof according to claim 15, wherein $R_2$ is H.

17. A compound or pharmaceutically acceptable salt thereof according to claim 15, wherein $R_2$ is OH, methyl, ethyl, i-propyl, $CH(CH_2OH)_2$, $CH(OH)CH_3$, OMe or $OCH_2CH_2OH$.

18. A compound or pharmaceutically acceptable salt thereof according to claim 1, wherein p is 2 and $R_3$ is H or $C_{1-6}$ straight or $C_{4-8}$ branched chain alkyl.

19. A compound or pharmaceutically acceptable salt thereof according to claim 1, wherein p is 2 and $R_3$ is H.

20. A compound or pharmaceutically acceptable salt thereof according to claim 1, wherein p is 2 and $R_3$ is methyl, ethyl, n-propyl, i-propyl or i-amyl.

21. A compound or pharmaceutically acceptable salt thereof according to claim 1, wherein p is 3 and $R_3$ is H or $C_{1-6}$ straight or $C_{4-8}$ branched chain alkyl.

22. A compound or pharmaceutically acceptable salt thereof according to claim 1, wherein p is 3 and $R_3$ is H.

23. A compound or pharmaceutically acceptable salt thereof according to claim 1, wherein p is 3 and $R_3$ is methyl, ethyl, n-propyl, i-propyl or i-amyl.

24. A compound or pharmaceutically acceptable salt thereof according to claim 1, wherein:

Ar is selected from phenyl, 2-or 3-thienyl, 2-or 3-furyl, 2-, 3-or 4-pyridyl and 2-, 4-or 5-thiazolyl;

$R_1$ is H;

$R_2$ is selected from H, OH, $CH_3$, $CH_2CH_3$, $CH(CH_3)_2$, $CH(CH_2OH)_2$, $CH(OH)CH_3$, $OCH_3$ and $OCH_2CH_2OH$;

$R_3$ is selected from H, methyl, ethyl, n-propyl, i-propyl and i-amyl; and p is 2 or 3.

25. A method for treatment of shock of hypovolemic or vasodilatory origin, bleeding esophageal varices, hepatorenal syndrome, cardiopulmonary resuscitation, anesthesia-induced hypotension, orthostatic hypotension, paracentesis-induced circulatory dysfunction, intraoperative blood loss or blood loss associated with burn debridernent and epistaxis, and of various ocular diseases by increasing laerimationitear formation, wherein said method comprises administering to an animal, including human, patient of a therapeutically effective amount of a compound according to claim 1, or a pharmaceutically acceptable salt thereof.

26. A method according to claim 25, wherein the animal is a human.

27. A method according to claim 26, wherein the disorder is shock of hypovolemic origin.

28. A method according to claim 26, wherein the disorder is shock of vasodilatory origin.

29. A method according to claim 26, wherein the disorder is bleeding esophageal varices.

30. A method according to claim 26, wherein the disorder is hepatorenal syndrome.

\* \* \* \* \*

UNITED STATES PATENT AND TRADEMARK OFFICE
CERTIFICATE OF CORRECTION

PATENT NO. : 8,778,881 B2
APPLICATION NO. : 13/409976
DATED : July 15, 2014
INVENTOR(S) : Kazimierz Wisniewski et al.

It is certified that error appears in the above-identified patent and that said Letters Patent is hereby corrected as shown below:

Title Page, Item (56)

Column 2, line 5 (Other Publications); delete ""Terlipression" and insert -- "Terlipressin --.

Column 2, line 5 (Other Publications); delete "terlipression" and insert -- terlipressin --.

Column 2, line 11 (Other Publications); delete "radomised" and insert -- randomised --.

Column 2, line 16 (Other Publications); delete ""Terlipression" and insert -- "Terlipressin --.

Column 2, line 16 (Other Publications); delete "nonrepinephrine-resistant" and insert -- norepinephrine-resistant --.

Column 2, line 18 (Other Publications); delete "Vasopression" and insert -- Vasopressin --.

Column 2, line 21 (Other Publications); delete "Vasopression" and insert -- Vasopressin --.

In the Claims

Column 39, lines 65-67; in claim 2, delete "2-or 3-thienyl, 2-or 3-furyl, 2-, 3-or 4-pyridyl and 2-, 4-or 5-thiazolyl" and insert -- 2- or 3-thienyl, 2- or 3-furyl, 2-, 3- or 4-pyridyl and 2-, 4- or 5-thiazolyl --.

Column 40, line 36; in claim 4, delete "accutable" and insert -- acceptable --.

Column 40, line 41; in claim 5, delete "OCH$_2$CH$_2$0H." and insert -- OCH$_2$CH$_2$OH. --.

Signed and Sealed this
Fifteenth Day of March, 2016

Michelle K. Lee
*Director of the United States Patent and Trademark Office*

CERTIFICATE OF CORRECTION (continued)
U.S. Pat. No. 8,778,881 B2

In the Claims

Column 41, line 28; in claim 24, delete "2-or 3-thienyl, 2-or 3-furyl, 2-, 3-or 4-pyridyl and 2-, 4-or 5-thiazolyl" and insert -- 2- or 3-thienyl, 2- or 3-furyl, 2-, 3- or 4-pyridyl and 2-, 4- or 5-thiazolyl --.

Column 42, line 12; in claim 25, delete "debridernent" and insert -- debridement --.

Column 42, line 13; in claim 25, delete "laerimationitear" and insert -- lacrimation / tear --.